United States Patent
Shin et al.

(10) Patent No.: US 7,521,590 B2
(45) Date of Patent: Apr. 21, 2009

(54) PHOSPHOLIPASE C β1 (PLCβ1) KNOCKOUT MICE AS A MODEL SYSTEM FOR TESTING SCHIZOPHRENIA DRUGS

(75) Inventors: Heesup Shin, Uiwang-si (KR);
Hae-Young Koh, Goyang-si (KR);
Daesoo Kim, Daejeon-si (KR); Sukchan Lee, Daejeon-si (KR)

(73) Assignee: Korea Institute of Science and Technology, Seoul (KR)

( * ) Notice: Subject to any disclaimer, the term of this patent is extended or adjusted under 35 U.S.C. 154(b) by 41 days.

(21) Appl. No.: 11/740,838

(22) Filed: Apr. 26, 2007

(65) Prior Publication Data

US 2008/0060088 A1    Mar. 6, 2008

Related U.S. Application Data

(60) Provisional application No. 60/824,384, filed on Sep. 1, 2006.

(51) Int. Cl.
*G01N 33/00* (2006.01)
*A01K 67/027* (2006.01)
*A01K 67/033* (2006.01)

(52) U.S. Cl. .............................. 800/18; 800/3; 800/14; 800/13

(58) Field of Classification Search ........................ None
See application file for complete search history.

(56) References Cited

OTHER PUBLICATIONS

Denning and Priddle. Reproduction 126:1, col. 2, par 1, 2003.*
Kim et al. Nature 389:290-293, 1997.*
Bohm et al. Molecular Cellular Neurosci 21:584-601, 2002.*
Miyakawa et al. PNAS 100(15):8989-8992, 2002.*
Strelets et al. Neuroscience and Behavioral Physiology 36(6):655-662, 2006.*
Shirakawa O et al., "Abnormal Neurochemical Asymmetry in the Temporal Lobe of Schizophrenia" Prog Neuropsychopharmacol Biol Psychiatry 25: 867-877, 2001.
Arinami T et al., "Genomewide High-Density SNP Linkage Analysis of 236 Japanese Families Supports the Existence of Schizophrenia Suceptibility Loci on Chromosomes 1p, 14q, and 20p" Am J Hum Genet 77:937-944, 2005.
Yee BK et al., "A Schizophrenia-related Sensorimotor deficit links α3-containing GABAA receptors to a dopamine hyperfunction" Proc Natl Acad Sci U.S.A. 102: 17154-17159, 2005.

* cited by examiner

*Primary Examiner*—Deborah Crouch
*Assistant Examiner*—Marcia S Noble
(74) *Attorney, Agent, or Firm*—Joseph Hyosuk Kim; JHK Law

(57) ABSTRACT

The present invention relates to a method for screening therapeutic drugs of schizophrenia using an animal model of the disease. More specifically, this invention relates to a screening method based on the phospholipase C β1 (PLCβ1) knockout mouse as an animal model of schizophrenia with all the major symptoms of the human disease. This knockout mouse exhibits symptoms similar to human schizophrenia such as locomotor hyperactivity, impaired prepulse inhibition of the startle response, lack of barbering and nesting behaviors, socially subordinate status, impaired learning, and lack of type II theta rhythm which has been implicated in working memory. Thus, the knockout mouse of the present invention can be useful as an animal for screening therapeutic drugs against schizophrenia.

2 Claims, 4 Drawing Sheets

PHOSPHOLIPASE C β1 (PLCβ1) KNOCKOUT MICE AS A MODEL SYSTEM FOR TESTING SCHIZOPHRENIA DRUGS

CROSS REFERENCE TO RELATED APPLICATIONS

This application claims the benefit of U.S. Provisional Application No. 60/824,384, filed Sep. 1, 2006, and claims foreign priority benefit to Korean Application No. 10-2006-0093541, filed Sep. 26, 2006. Each of the above-referenced prior applications is incorporated by reference herein in their entireties and hereby made a part of this specification.

FIELD OF THE INVENTION

The present invention relates to a method for screening therapeutic drugs against schizophrenia using a gene-knockout animal model. More specifically, the present invention relates to a phospholipase C β1 (PLCβ1) knockout mouse exhibiting major symptoms of schizophrenia and a screening method using the same.

BACKGROUND OF THE INVENTION

Schizophrenia is a psychiatric disorder with wide-ranging symptoms such as positive symptoms including delusion, hallucination and disorganized speech; negative symptoms including affective flattening, avolition, poverty of speech and social withdrawal; and cognitive impairment including deficits in attention, planning and abstract thinking and short and long term memory (Andreasen, N. C. et al, *Lancet* 346: 477~481, 1995; Lewis, D. A., Liebermann, J. A., *Neuron* 28: 325~334, 2000). The lifetime prevalence of schizophrenia is about 1%, which, in a global scale, amounts to 10 million sufferers. Family, twin, and adoption studies show that there is a relation between the lifetime risk for schizophrenia and genetic factors. This significant role that genetic factors play in the pathogenesis of schizophrenia was shown in linkage studies that identified strong candidate susceptibility genes and their loci (Gogos, J. A., Gerber, D. J., *Trends Pharmacol. Sci.* 27: 226~233, 2006). Carriers of these candidate genes, however, do not necessarily exhibit the symptoms. Thus, these facts indicate that complex, interdependent genetic factors are involved in the connection between susceptibility genes and a full-blown disease. It is speculated that these genes may exert diverse influence on the core system so as to functionally heighten schizophrenia risks (Harrison, P. J., Weinberger, D. R., *Mol. Psychiatry* 10: 40~68, image 45, 2005).

Animal models are important tools in understanding the neurobiology of complex brain diseases and serve as test subjects against which therapeutic efficacy of new drugs are evaluated. An animal model should display relevant endophenotypes, and the corresponding endophenotypes for a schizophrenia model would be locomotive hyperactivity, sensorimotor gating deficits, deficits in social interaction, and such cognitive impairments as in learning and memory (Braff, D. L., Freedman, R., *Endophenotypes in studies of the genetics of schizophrenia*. Lippincott Williams & Wilkens, 2002; Gould, T. D., Gottesman, I. I., *Genes Brain Behav.* 5: 113-119, 2006; van den Buuse, M. et al, *Aust. NZ. J. Psychiatry* 39: 550~557, 2005).

Based on either current pathophysiological hypotheses (e.g. dopamine hypothesis) or known genetic linkages of schizophrenia, a few genetically modified mice targeting candidate susceptibility genes have so far been generated as animal models. These mouse models display at least one or more of the endophenotypes listed above (Gainetdinov, R. R. et al, *Trends Neurosci.* 24: 527~533, 2001; Gerber, D. J. et al. *Proc. Natl. Acad. Sci.* 98: 15312~15317, 2001; Kellendonk, C. et al., *Neuron* 49: 603~615, 2006; Lijam, N. et al, *Cell* 90: 895~905, 1997; Robertson, G. S. et al, *J. Psychiatry Neurosci.* 31: 157~167, 2006; Yee, B. K. et al, *Proc. Natl. Acad. Sci.* 102: 17154~17159, 2005); however, animal models simultaneously having multiple endophenotypes have not been developed.

Meanwhile, phospholipase C β1 (PLCβ1) hydrolyzes phosphatidylinositol 4,5-bisphosphate to yield diacyl-glycerol and inositol 1,4,5-trisphosphate ($IP_3$), second messengers in the PLCβ1 signaling. β1 is the phospholipase C β isoform associated with G-protein-coupled receptors (GPCRs), which are known to be involved in many central nervous system (CNS) functions. PLCβ1 is expressed in select areas of brain such as cerebral cortex, hippocampus, amygdala, lateral septum, and olfactory bulbs (Watanabe, M. et al, *Eur. J. Neurosci.* 10: 2016~2025, 1998). Such an expression profile suggests its implication in diverse critical brain functions including cognitive ones. Besides, a possible genetic association with schizophrenia has been reported in a linkage study of 20p12 (Arinami, T. et al, *Am. J. Hum. Genet.* 77: 937~944, 2005), and abnormal expression patterns were observed in the brains of schizophrenics (Shirakawa, O. et al, *Prog. Neuropsychopharmacol. Biol. Psychiatry* 25: 867~877, 2001).

With this supporting information at hand, the present inventors have developed a phospholipase C β1 knockout mouse (PLCβ1−/−) and confirmed its utility as an animal model of schizophrenia by carrying out various behavioral and neurological tests.

DETAILED DESCRIPTION OF THE INVENTION

The present invention provides a screening method for prophylactic or therapeutic drugs of schizophrenia using a mouse model expressing schizophrenic symptoms wherein the gene for phospholipase C β1 is knocked out.

The inventive screening method for prophylatic and therapeutic drugs of schizophrenia involve the following steps:

1) treating the phospholipase C β1 knockout mouse of this invention that expresses schizophrenic symptoms with a candidate drug;

2) monitoring schizophrenic endophenotypes of the knockout mouse of step 1) after the treatment of the candidate drug;

3) selecting candidate drugs which significantly reduce the expression of schizophrenic endophenotypes by comparing the treated knockout mice of step 2) with untreated control knockout mice of this invention.

Since the genetics of schizophrenia involve multiple factors and a complex susceptibility profile, valid animal models are vital in the studies to decipher biological underpinnings of this disease. With this in mind, the present inventors have chosen the gene for phospholipase C β1 (PLCβ1) among the candidate susceptibility genes associated with schizophrenic endophenotypes and developed a knockout mouse model of schizophrenia (Kim, D. et al, *Nature* 389:290~293, 1997; Korean Patent Registration No. 372843). PLCβ1 is expressed in select areas of brain such as cerebral cortex, hippocampus, amygdala, lateral septum, and olfactory bulbs, implicating the enzyme in diverse critical brain functions including cognition. Considering that major cognitive dysfunction is the hallmark of schizophrenia, we examined the possibility of PLCβ1 knockout mice (PLCβ1−/−) as an animal model for this psychiatric disorder by performing various behavioral and neurological tests (general locomotor activity, sensorimotor gating, social behaviors, learning and memory).

First, in open-field tests for locomotor activity, wild-type and PLCβ1−/− mice were monitored for a period of an hour in 5-minute intervals with a digital video recorder. As shown in FIG. 1, PLCβ1−/− mice displayed an increase in locomotion relative to wild-type mice. The total distance traveled by a PLCβ1−/− mouse in 1 hour was considerably longer than that of a wild-type mouse. In acoustic startle response tests for prepulse inhibition (PPI), PLCβ1−/− mice showed significantly reduced PPI (See FIG. 2, filled circles, knockout vs wild-type). This deficit in PPI by the knockout mice was reversed upon a treatment with the anti-psychotic drug, haloperidol to a level not significantly deviating from that of wild type treated with either haloperidol or saline (See FIG. 2C, haloperidol vs vehicle). Thus the anti-psychotic drug haloperidol was confirmed to be still effective towards PLCβ1−/− mice.

To look for the nesting behavior of PLCβ1−/− mice, cotton pieces were abruptly added as a nesting material to a cage covered flat with wood flakes containing either a wild-type or PLCβ1−/− mouse and photographs were taken 1 hour later. The results showed that whereas wild-type mice made fluffy nests out of the cotton pieces provided, PLCβ1−/− mice did not build anything (See FIG. 4).

As to whisker trimming, a social behavior observed in most male and female mice, no long whiskers were observed in most male and female wild-type mice (See FIG. 3A, left); in contrast, all PLCβ1 mice had long whiskers (FIG. 3A, right). The relative amount of long whiskers after 3 months was far greater in PLCβ1−/− mice than wild-type (FIG. 3B, +/+;+/+, −/−;−/−). When a wild-type and a PLCβ1−/− mouse were placed in the same cage, the wild-type mouse had whiskers as long as those of a PLCβ1−/− mouse pair sharing a cage, whereas the PLCβ1−/− mouse had whiskers as short as those of a wild-type mouse pair sharing a cage (FIG. 3B, +/+;−/−). These results indicate that wild-type mice trimmed whiskers of their mates, but PLCβ1−/− mice failed to reciprocate. Such lack of barbering behavior translates to limited social interactions in PLCβ1−/− mice. In tests for social dominance, PLCβ1−/− mice lost to wild-type mice more often than by chance, indicating that wild-type mice are socially dominant over PLCβ1−/− mice.

In addition, Morris water maze tests revealed a lack of theta rhythm, which is known to be involved in impairments in diverse cognitive functions including spatial learning and memory (Shin, H. et al, 2005).

As described above, the knockout mouse of the present invention demonstrated: (1) an enhanced locomotor activity in the open-field test, (2) impaired prepulse inhibition (PPI) of the startle response, (3) lack of barbering and nesting behaviors, (4) socially subordinate trait, (5) impaired learning in the Morris water maze test, and (6) a lack of type-II theta rhythm involved in working memory. Since such features of the knockout mouse resemble schizophrenic symptoms, this mouse is likely to find use as an animal model for schizophrenia. The disease model of the present invention applies to mammals, preferably mice, rats, pigs, monkeys and apes, but by no means limited thereto.

Furthermore, as noted above, the prepulse inhibition deficits in PLCβ1−/− mice are completely reversed by systemic administration of haloperidol, a D2 receptor antagonist. This demonstrates that the present invention is not only useful as an animal model in neurobiological studies but can also be used in screening new therapeutic drugs for schizophrenia, in which brain functions are disrupted.

BRIEF SUMMARY OF THE INVENTION

The present invention provides an animal disease model for schizophrenia in which major schizophrenic endophenotypes are simultaneously expressed in the form of phospholipase C β1 knockout (PLCβ1−/−) mouse. The knockout mouse of the present invention is also useful for screening therapeutic drugs of schizophrenia.

EXAMPLES

The present invention is further described in detail by reference to the following experimental examples. These examples are provided for purposes of illustration only, and are not intended to be limiting unless otherwise specified.

Example 1

Construction and Rearing of the Knockout Mouse

The generation of PLCβ1−/− mice and the genotyping method are as described in Kim et al. (*Nature* 389:290~293, 1997). F1 homozygous mice and wild-type littermates were obtained by crossing C57BL/6J(N8)PLCβ1+/− and 129S4/Svjae(N8)PLC β1+/− mice. All animal care and handling were in observance of the institutional guidelines of the Korea Institute of Science and Technology (KIST). Mice were maintained with free access to food and water under a 12-hour light/dark cycle with light beginning at 6:00 AM.

Example 2

Locomotor Activity in Open-Field Tests

Each mouse (~10 weeks old) was gently placed at the center of an open-field test kit (40×40×50 cm white acrylic rectangular box, custom made) to start the test. Locomotor activity in the kit during 1-hour period was monitored in 5-minute intervals via digital video recording. The tests were carried out between 9:00~15:00 during the day.

The tests showed that the distance traveled by PLCβ1−/− mice was substantially longer than wild-type, indicating an increased locomotor activity for the knockout mouse. Habituation to new environment was similar in both types of mice.

Example 3

Tests for the Prepulse Inhibition (PPI) of Aural Startle Response

PPI tests were carried out with 26 responder mice 13~15 weeks old by using a single acoustic startle chamber (Coulbourn Instruments, USA), one mouse at a time. The startle reflex was triggered by a pulse stimulus in the form of a 40 msec, 120 dB burst of white noise (SS). Inhibition of the SS-elicited startle response was achieved using a 20 msec-prepulse stimulus of various intensities (74, 82, and 90 dB white noise) that preceded SS by 100 msec.

The test was composed of a series of 7 blocks, each of which was a "semi-random" mixture of 8 different trial types (no stimulus, SS only, three PP only, three PP plus SS), separated by 10 to 15-second intertrial intervals. The percent prepulse inhibition (%PPI) was calculated as [1−(response to PP-SS coupling/response to SS only)]×100.

Haloperidol (0.2 mg/kg body weight) was intraperitonealy (i.p.) administered 45 minutes before the test, using 0.5% dimethylsulfoxide (DMSO) in saline (0.9% NaCl) as the vehicle. Haloperidol (Tocris Cookson, UK) stock solution was prepared in DMSO and stored at 20° C. for less than a month.

Figure 1:
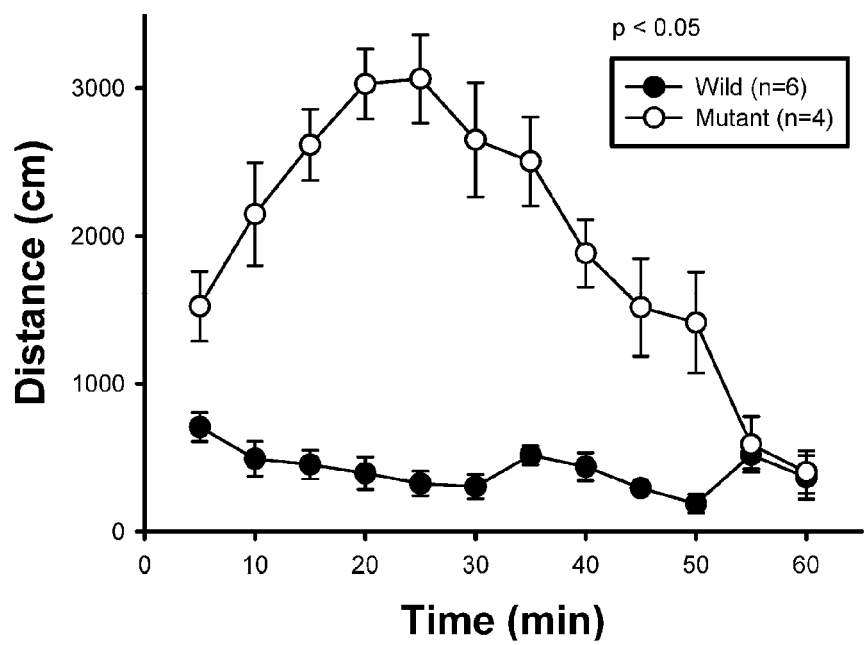
FIG. 1 shows the increased locomotive activity of PLCβ1 −/− mice.
Figure 2:
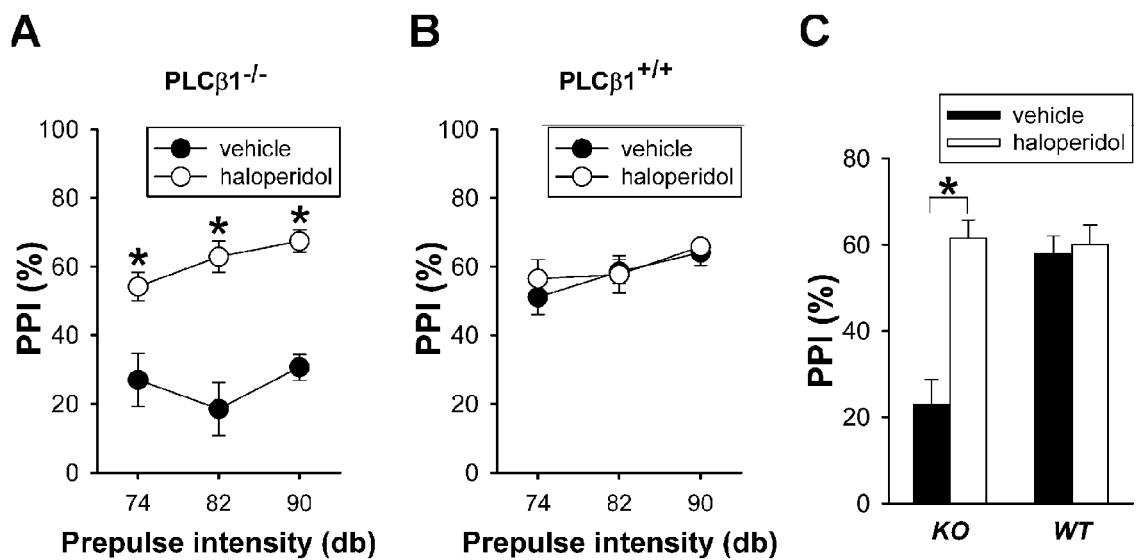
FIG. 2 exhibits a reversal of the prepulse inhibition (PPI) deficit in PLCβ1−/− mice effected by haloperidol, an antipsychotic drug.

In pulse-alone trials, the startle response of PLCβ1$^{-/-}$ mice was not significantly different from that of wild-type mice ($p>0.05$). Since there was no significant effect on the PPI magnitude of prepulse intensity level in either of the genotypes (FIGS. 1A, B), the PPI values at all the three prepulse intensities were lumped together and averaged (FIG. 2C). A significant attenuation of PPI was observed in PLCβ1$^{-/-}$ mice compared to wild-type mice (black bars, KO vs. WT, $p<0.05$). There was a significant effect of haloperidol (dopaminergic D2 receptor antagonist) on the PPI in PLCβ1$^{-/-}$ mice at all prepulse levels ($p<0.05$, FIG. 2A, C, KO) (n=5 and 7 for vehicle and haloperidol, respectively), but not in wild-type mice (FIG. 2B, C, WT) (n=8 and 6 for vehicle and haloperidol, respectively). Indeed, the PPI deficit in PLCβ1$^{-/-}$ mice was reversed by haloperidol so that the PPI value in the PLCβ1$^{-/-}$ mice treated with haloperidol was not significantly different from those in wild-type mice treated with either vehicle alone or haloperidol ($p>0.05$, FIG. 2C). The differential expression of haloperidol effect on PPI suggests an underlying dopamine hyperfunction in PLCβ1$^{-/-}$ mice that increased the responsiveness to the drug at a dose not effective in wild-type mice.

Example 4

Tests for Nesting Behavior

In the past, we noticed through a casual inspection of mice cages housing uniform genotypes that wild-type mice always built fluffy nests with the wooden flakes provided, at one of the corners of the cage floor, whereas PLCβ1$^{-/-}$ mice did not build anything. Based on this preliminary observation, we tested nesting behavior using commercial cotton nesting material acutely provided in the cage.

Figure 4:
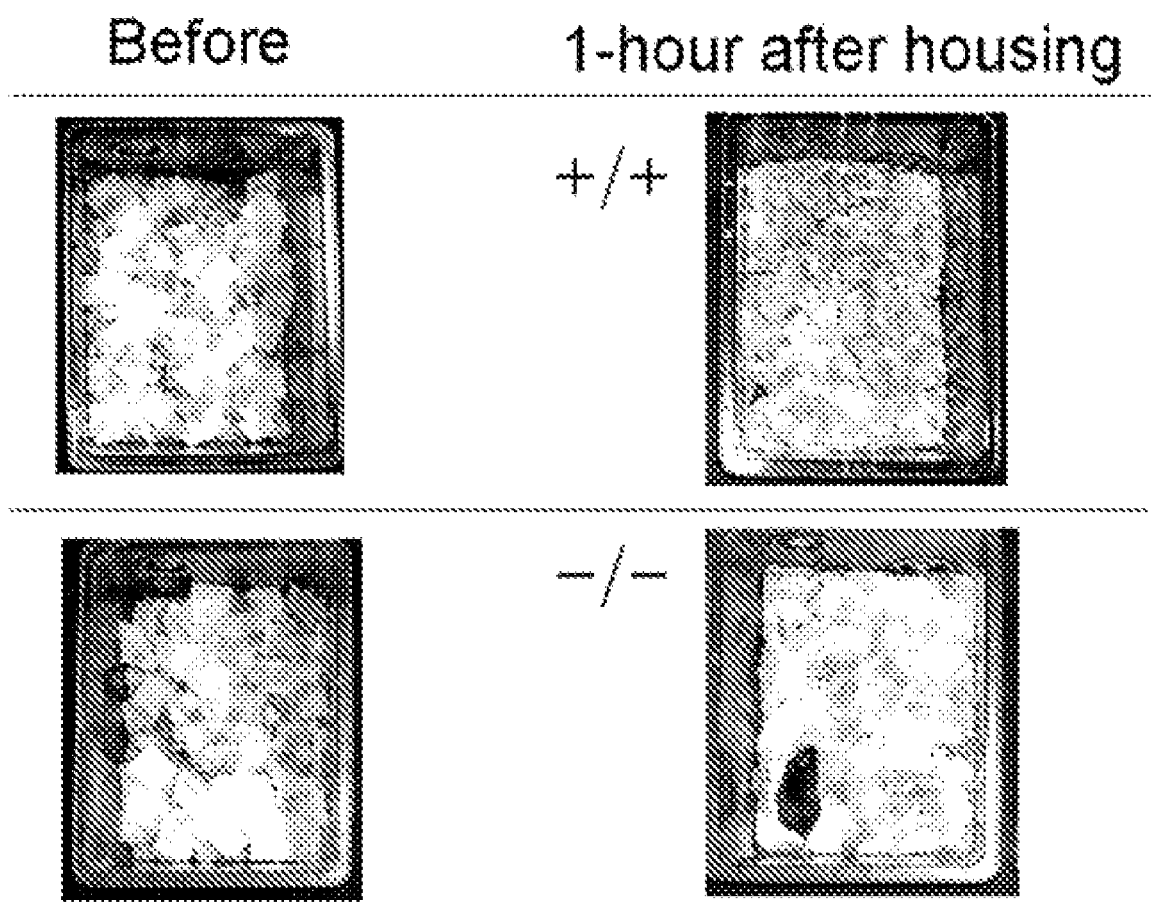
FIG. 4 indicates an apparent lack of nesting behavior in PLCβ1−/− mice.

Each of 9 wild-type and 9 PLCβ1$^{-/-}$ mice was placed alone in a cage evenly covered with wooden flakes and was provided with pieces of cotton nesting material sizing 5 cm×5 cm. An hour later, photographs were taken of the floor of each cage to inspect whether there was a nest made of the cotton material. Within an hour after being placed in a cage with the cotton pieces, each of the 9 wild mice tested built a nest, but none of the 9 PLCβ1$^{-/-}$ mice tested followed suit (FIG. 4).

Example 5

Tests for Barbering Behavior

Figure 3:
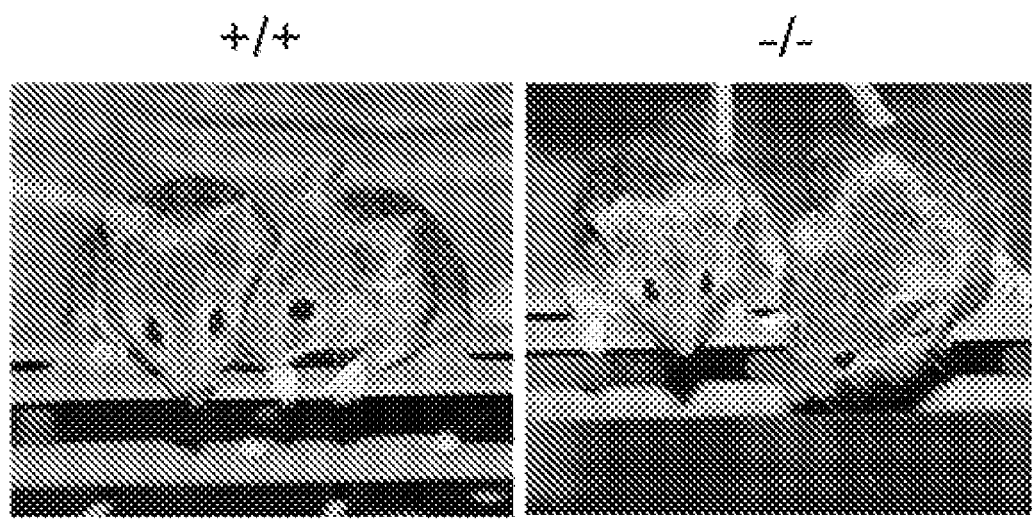
FIG. 3 shows long whiskers in wild-type and PLCβ1−/− mice indicating an apparent lack of barbering behavior among PLCβ1−/− mice.
Figure 3:
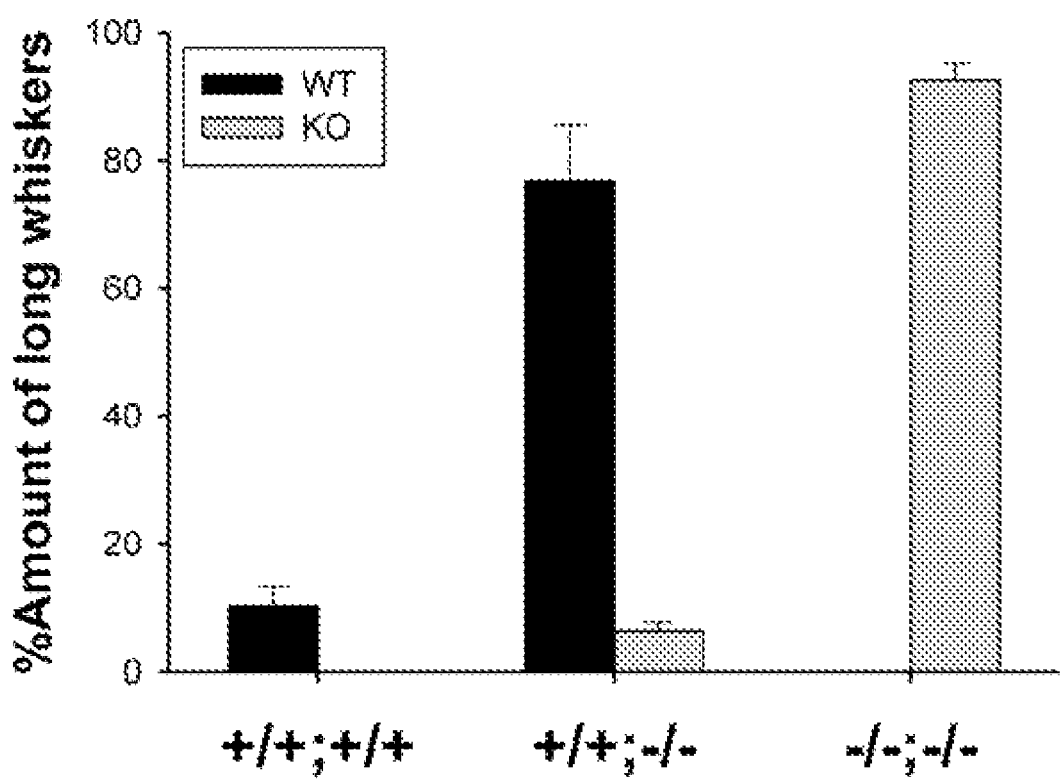

Whisker trimming is a social behavior observed in most mice, both male and female, among many of the commonly used strains (Strozik, E., Festing, M. F., Lab. Anim. 15:309~312, 1981). This behavior may be one of the endophenotypes relevant to the social withdrawal shown in schizophrenia patients. A casual inspection of pairs of the offspring sharing the same genotype housed in the same cage revealed that most wild-type male and female mice were completely devoid of long whiskers (FIG. 3A, left); however, all PLCβ1$^{-/-}$ mice had full sets of long whiskers (FIG. 3A, right). In addition, at the age of weaning, both PLCβ1$^{-/-}$ and wild-type mice had full sets of long whiskers; however, as wild-type mice grew older, they lost their long whiskers. Wild-type and PLCβ1$^{-/-}$ mice housed in couples of either uniform or mixed genotypes were scored for the presence of whiskers longer than 0.5 cm at 3 months of coupling. In the uniform genotype housing, the relative amount of long whiskers was significantly greater for PLCβ1$^{-/-}$ mice than wild-type (FIG. 3B, +/+;+/+, −/−;−/−). In the mixed genotype housing, the wild-type mouse had as many long whiskers as any uniform-coupled PLCβ1$^{-/-}$ mouse, but the PLCβ1$^{-/-}$ mouse had as few long whiskers as any uniform-coupled wild-type mouse (FIG. 3B, +/+;−/−), demonstrating that wild mice trimmed the whiskers of their inmates, but PLCβ1$^{-/-}$ mice did not. These results suggest such lack of barbering behavior in PLCβ1$^{-/-}$ mice may correlate with low levels of social interaction of schizophrenics.

Example 6

Tests for Social Dominance

The kit for social dominance test was made of transparent acryl. Two 10×10×10 cm-waiting chambers were connected through a 30×3×3 cm-tube between them with sliding doors at the openings to each chamber. A wild-type and a PLCβ1$^{-/-}$ mouse of the same gender were put in each of the waiting chambers, and then released by removing the doors. A subject mouse was defined the "winner" when it remained at its place or moved forward as its opponent backed out of the tube (Messeri, P., Eleftheriou, B. E., Oliverio, A., Physiol. Behav. 14:53~58, 1975)

Figure 5:
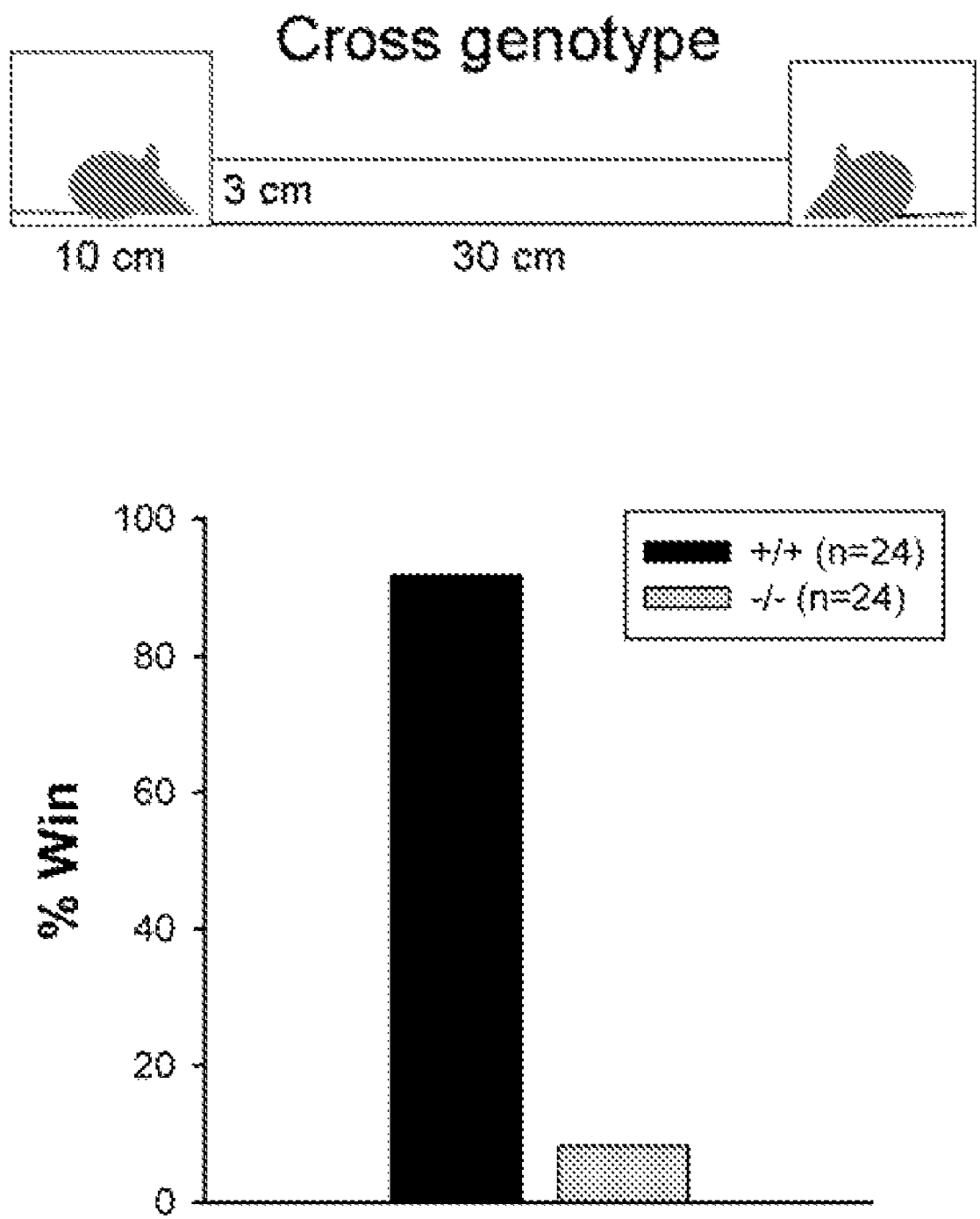
FIG. 5 is a graph showing the test results from the social dominance tube kit. Wild-type mice are socially dominant over PLCβ1−/− mice.

Each mouse was tested twice with an opponent of the same gender with the other genotype. PLCβ1$^{-/-}$ mice lost more bouts than expected by chance ($p<0.05$, FIG. 5), demonstrating the social dominance of wild-type over PLCβ1$^{-/-}$ mice.

INDUSTRIAL APPLICABILITY

The PLCβ1 knockout mouse of the present invention exhibits endophenotypes similar to those of human schizophrenia including i) locomotor hyperactivity, ii) impaired prepulse inhibition of the startle response, iii) a lack of barbering and nesting behaviors, iv) a socially subordinate status, v) impaired learning as observed in Morris water maze test, and vi) a lack of type II theta rhythm which has been implicated in working memory. Thus, the knockout mouse of the present invention can be an effective animal model for deciphering the multifactorial pathogenesis as well as screening therapeutic drugs of schizophrenia.

What is claimed is:

1. A screening method for identifying a candidate drug for the treatment of schizophrenia comprising:
   1) providing a first and second transgenic mouse wherein the first and second transgenic mouse comprise a homozygous disruption of the phospholipase Cβ1 (PLCβ1) gene in its genome, wherein the first and second transgenic mouse do not express PLCβ1, and wherein the first and second transgenic mouse comprise phenotypic behaviors associated with schizophrenia;

2) administering a candidate drug to the first transgenic mouse; and 3) comparing the behavior associated with schizophrenia in said first transgenic mouse administered the candidate drug to the behaviors associated with schizophrenia in said second transgenic mouse that did not receive the candidate drug, wherein a reduction in behaviors associated with schizophrenia in said first transgenic mouse as compared to the second transgenic mouse identifies the candidate drug as a therapeutic drug for schizophrenia.

2. The screening method according to claim 1, wherein the phenotypic behaviors associated with schizophrenia are one or more of the following: (a) locomotor hyperactivity; (b) a deficit in prepulse inhibition of the startle response; (c) a lack of barbering and/or nesting behavior; (d) a socially submissive trait; (e) a learning deficit; and (f) a lack of type-II theta rhythm.

* * * * *